United States Patent [19]

Huang

[11] 4,328,129

[45] May 4, 1982

[54] CATALYST FOR MAKING DIMETHYL ETHER AND METHANOL FROM SYNTHESIS GAS

[75] Inventor: Yun-Yang Huang, Troy, Mich.

[73] Assignee: Ethyl Corporation, Richmond, Va.

[21] Appl. No.: 103,750

[22] Filed: Dec. 14, 1979

[51] Int. Cl.³ .................. B01J 21/04; B01J 23/64; B01J 23/88
[52] U.S. Cl. .................................................. 252/465
[58] Field of Search .......................... 252/465, 470; 260/449 R

[56] References Cited

U.S. PATENT DOCUMENTS

| | | | |
|---|---|---|---|
| 3,523,966 | 8/1970 | Ottman et al. | 252/465 X |
| 3,840,471 | 10/1974 | Acres | 252/470 X |
| 3,933,623 | 1/1976 | Durkin et al. | 252/470 X |
| 4,061,713 | 12/1977 | Weidenbach et al. | 252/466 PT |
| 4,210,597 | 7/1980 | Huang | 252/465 X |

*Primary Examiner*—W. J. Shine
*Attorney, Agent, or Firm*—Donald L. Johnson; Joseph D. Odenweller; Teresa M. Stanek

[57] ABSTRACT

A process for selectively preparing dimethyl ether and methanol by contacting a gaseous mixture containing carbon monoxide and hydrogen with a rhodium-molybdenum catalyst at reaction conditions correlated so as to favor the formation of a substantial proportion of these products.

3 Claims, No Drawings

CATALYST FOR MAKING DIMETHYL ETHER AND METHANOL FROM SYNTHESIS GAS

BACKGROUND OF THE INVENTION

This invention relates to a Fischer-Tropsch reaction. More particularly, this invention relates to a process for the selective conversion of synthesis gas to dimethyl ether and methanol by continuously passing a feed stream of carbon monoxide and hydrogen over a supported rhodium-molybdenum catalyst at reaction conditions correlated to produce such products.

It is known in the art to react carbon monoxide and hydrogen to produce dimethyl ether and methanol. For example, U.S. Pat. No. 3,941,819 discloses a process for the production of substantial amounts of dimethyl ether by passing carbon monoxide and hydrogen over platinum supported on alumina at a temperature ranging from 100° C. to 400° C. and a pressure ranging from 1 to 100 atmospheres. U.S. Pat. No. 4,098,809 discloses that dimethyl ether can be prepared by feeding a mixture of CO, $CO_2$ and $H_2$, wherein the quantity of CO is in excess of the stoichiometric value, to a reactor containing a methyl alcohol synthesis catalyst, such as a copper base or chrome-zinc base catalyst, a methyl alcohol dehydration catalyst, such as alumina, whereby methyl alcohol is formed as an intermediate product which is transformed into dimethyl ether in the same reactor at a temperature in the range of 220° C. to 400° C. and a pressure in the range of 30 to 500 kg/cm$^2$. The hydrogenation of carbon monoxide over supported palladium catalysts to yield methanol in high selectivity is reported by Poutsma et al., "J. Catalysis," vol. 52, (1978), pp. 157-160. In a recently published study by Bhasin et al., "J. Catalysis," vol. 54, (1978), p. 120, there is reported the formation of methanol in large amounts when synthesis gas is contacted with a rhodium-iron catalyst.

SUMMARY OF THE INVENTION

This invention provides a method for selectively producing dimethyl ether and methanol from gaseous mixtures of carbon monoxide and hydrogen. The process of the invention involves contacting synthesis gas with a catalyst comprising rhodium in combination with molybdenum upon a support material under suitable reaction conditions.

DESCRIPTION OF THE PREFERRED EMBODIMENTS

According to the present invention, a gaseous mixture of carbon monoxide and hydrogen is contacted, in a reaction zone with a catalyst comprising rhodium and molybdenum supported on alumina under reactive conditions of temperatures, pressure, gas composition and space velocity correlated so as to favor the formation of a substantial proportion of dimethyl ether and methanol. Thus, a preferred embodiment of the present invention is a process for selectively producing dimethyl ether and methanol which comprises the step of contacting a gaseous mixture containing carbon monoxide and hydrogen with a catalyst comprising rhodium and molybdenum supported on alumina at reaction conditions correlated so as to favor the formation of a substantial proportion of such products.

The catalyst used in the practice of this invention is believed novel and its constituents different from those of the prior art. Such a catalyst exhibits enhanced selectivity for the production of dimethyl ether and methanol from synthesis gas. The catalyst according to this invention comprises rhodium and molybdenum supported on alumina. Thus another embodiment of the present invention is a catalyst for selectively converting gaseous mixtures of carbon monoxide and hydrogen to dimethyl ether and methanol, said catalyst comprising rhodium and molybdenum supported on alumina.

PROCESS DISCUSSION

The reaction is conducted at more or less conventional Fischer-Tropsch reaction conditions of temperature, pressure, gas composition and space velocity so that conventional technology and equipment may be used. Overall, the reaction is conducted at reactive conditions of temperature, pressure, gas composition and space velocity which are correlated to achieve optimal selectivity for dimethyl ether and methanol. The reaction efficiency, or selectivity, to dimethyl ether and methanol is invariably at least about 25% and is usually upwards of about 45%. Under preferred conditions it exceeds 50% and under optimal conditions, can reach approximately 60%. Selectivity is defined herein as the percentage of carbon atoms converted from carbon monoxide to a specified compound or compounds including carbon dioxide.

The reaction is highly exothermic with the thermodynamic equilibrium and kinetic reaction rates being governed by the reaction temperature. Average catalyst bed temperatures are usually within the range of about 180° C.-300° C.

The reaction temperature appears to be an important process variable affecting not only activity but selectivity toward the desired products. Generally, with all other variables held constant, the efficiency of dimethyl ether and methanol production is greatest at temperatures near the lower end of the temperature range, i.e. approximately 190° C.-220° C. Generally, total synthesis gas conversion increases as temperature increases over the temperature range. At the same time, however, higher temperatures favor increased $CO_2$ production.

In the above description, the indicated temperatures are expressed as average, or mean reaction bed temperatures. Because of the tendency for smaller amounts of dimethyl ether and methanol to be formed at the higher reaction temperatures, it is desirable for the purposes of the present invention that for optimal selectivity to dimethyl ether and methanol production that temperature be controlled so as not to exceed approximately 275° C., and more preferably about 250° C.

The reaction zone pressure is desirably within the range of about 50 psig to about 5000 psig. Generally, at higher reaction zone pressures the selectivity for methanol production is greater than for dimethyl ether. Conversely, lower reaction pressures favor the formation of more dimethyl ether than methanol.

The ratio of hydrogen to carbon monoxide in the synthesis gas may vary somewhat. Normally, the mole ratio of hydrogen to carbon monoxide is within the range of 4:1 to 1:4 and preferably within the range of 2:1 to 1:2.

Conversion is conveniently achieved by employing a high space velocity correlated with other reaction variables (e.g. temperature, pressure, gas composition, catalyst, etc.) Space velocity of from about 500 to 10,000 gas hourly space velocities (volumes of reactant gas at 0° C. and 760 mm mercury pressure per volume of catalyst per hour) are generally employed. A typical gas hourly space velocity used in the practice of the present process is about 1200 GHSV.

THE CATALYST

The rhodium-molybdenum components of the present invention catalyst are provided in combination upon a support material. This is typically effected by depositing rhodium and molybdenum onto a support material and placing the supported combination into the reaction zone. For purposes of this invention, the catalyst composition may additionally contain approximately 3.0 percent by weight iron. As illustrated below, a catalyst composition comprising approximately 3.0 weight percent iron, 3.0 weight percent rhodium and 6.5 weight percent molybdenum was found to have about the same selectivity for dimethyl ether and methanol formation as a catalyst composition comprising about 3.0 weight percent rhodium and 6.5 weight percent molybdenum. Activity of the iron containing catalyst, however, was somewhat less.

On the basis of experience to date, the quantities of metals on the support should range from about 0.1 weight percent to about 10.0 weight percent for the rhodium and from about 1.0 weight percent to about 30 weight percent for the molybdenum, based on the combined weight of the metal and the support material. Preferably, the amount of rhodium and molybdenum metals on the support are within the range of about 1.5 to 5.0 weight percent and 3.0 to 15.0 weight percent, respectively. Generally, activity and selectivity for dimethyl ether and methanol production increase as the molybdenum concentration in the catalyst compositions is increased.

The carrier substrate is preferably a high surface area material of the type conventionally employed in the preparation of heterogenous catalyst systems. The substrate material nominially has a surface area of at least about 100 square meters per gram. $\gamma$-alumina is a highly preferred carrier substrate material for the preparation of the present invention rhodium-molybdenum catalysts. The use of $\gamma$-alumina as a support material suggests that other carrier substrate materials such as alpha-alumina, eta-alumina, silica, silica-alumina, magnesia, carbon, zeolites and the like may also function as suitable support materials in the practice of the present invention.

The rhodium and molybdenum may be deposited onto the base or support by any of the techniques commonly used for catalyst preparation, as for example, impregnation from an organic or inorganic solution, precipitation, coprecipitation, or cation exchange. Conveniently, a solution of a heat decomposable inorganic or organic rhodium compound and a solution of a heat decomposable molybdenum compound is appropriately contacted with the support material, and the support then dried and heated, the latter advantageously under reducing conditions, to form a finely dispersed rhodium-molybdenum supported catalyst. The rhodium and molybdenum may be deposited concurrently or sequentially. Illustrative of water-soluble compounds are the chloride and nitrate salts of rhodium and ammonium paramolybdate.

In a preferred method of catalyst preparation, supports were impregnated with an aqueous solution of the appropriate quantity of a water-soluble molybdenum compound. The amount of solution impregnated was an amount just sufficient to completely cover or wet the support. The impregnated carrier substrate material was then subjected to drying conditions to lower the water content of the resultant catalyst composition to the lowest possible level. In a typical drying procedure, the composition was first air-dried at room temperature for 2-3 days. It was then placed in an oven and heated at a temperature of approximately 100° C. for approximately 2 hours. The catalyst composition was then calcined by slowly heating the composition up to a temperature between about 500° C. and 600° C. over a period of several hours and then holding the composition at this final temperature for approximately 12-15 hours. The composition was then cooled to room temperature and thereafter impregnated with an aqueous solution of an appropriate quantity of a water soluble rhodium compound. The amount of solution used was just enough to completely cover or wet the molybdenum impregnated composition. The co-impregnated carrier substrate material was then subjected to drying conditions to lower the water content of the resultant catalyst composition to the lowest possible level. Typically, the mixture was dried at room temperature for about 2-3 days and/or dried slowly over a hot plate until all of the liquid had evaporated. The composition was then placed in an oven and dried at 100° C. for about 2 hours. The doubly impregnated composition was then calcined by slowly heating the composition up to a temperature between about 500° C. and 600° C. over a period of several hours and then heating the composition at this temperature for about 12-16 hours. If a chloride salt of rhodium was used, it was found advantageous to mildly reduce the composition with hydrogen prior to calcining in order to insure that sublimation of the compound did not occur. This was accomplished by flowing hydrogen over the composition while slowly heating the composition from about 200° C. to about 300° C. over a period of time of from 2 to 3 hours.

As a further required step in the procedure for catalyst preparation, the dry-state catalyst composition was reduced with hydrogen. It was found advantageous to reduce the rhodium and molybdenum compounds by contacting the catalyst composition with hydrogen, and then heating the catalyst reduction zone slowly from room temperature up to about 400° C. over a period of several hours (typically 6-7 hours). The catalyst composition was then maintained at this elevated temperature limit for an additional 15-17 hours.

If a rhodium-molybdenum catalyst composition prepared and reduced as described above was charged to a synthesis gas conversion zone, then the selective yield of desirable dimethyl ether and methanol products was obtained, provided the aforestated reaction conditions were observed.

DESCRIPTION OF TEST REACTOR

The reactors used in these studies were either a stainless steel tubular flow reactor or a bottom-agitated "Magnedrive" autoclave of the J. M. Berty design with a centrally positioned catalyst basket and a side product effluent line.

The tubular flow reactor consisted of a stainless steel tube 14 inches in length having an internal diameter of 0.775 centimeters; an outside wall diameter of 0.953 centimeters; and a wall thickness of 0.089 centimeters. The catalyst bed had a volume of approximately 5 cubic centimeters.

The autoclave of the J. M. Berty design was of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology-Part II, Sixty Fourth National Meeting of the American Institute of Chemical Engineers (AIChE), at New Orleans, La., on Mar. 16-20, 1969 and obtainable from AIChE at 345 East 47 Street, New York, N.Y, 10017. A variable speed, externally driven fan continuously recirculated the reaction mixture over the centrally positioned catalyst bed. The autoclave was stainless steel having an interior volume of about 400 cubic centimeters. A feed gas stream containing hydrogen and carbon monoxide was introduced at the bottom of the autoclave through the well for the shaft of the Magnedrive agitator. The reactor was modified so that effluent gas samples could be taken in a glass bulb right after the gas had been released to atmospheric pressure. Liquid products were condensed in a trap by cooling water at the high pressure end of the effluent. No additional cryogenic trap was employed. The non-condensable components of the exit stream were sampled periodically at the exit port and analyzed by gas chromatography. Hydrogen and carbon monoxide flow was controlled and measured by separate flow meters.

DESCRIPTION OF THE TEST PROCEDURE

The bulk volume of a weighed catalyst sample was determined, and the sample was placed in the reactor. The quantity of catalyst charged to the reactor was typically 3 to 4 grams. Thin layers of glass wool were placed above and below the catalyst bed to prevent circulation of solid fines. The reactor was then sealed and the process lines were pressure tested at ambient temperature to a pressure about 500 to 1000 psig in excess of the maximum anticipated working pressure. Hydrogen was used for this test.

When the reactor was shown to be leak-free, pure hydrogen was passed through the reactor, and the temperature was raised slowly from room temperature to about 400° C. in the tubular flow reactor (250° C. in the Berty reactor) over a period of several hours (typically 5–7 hours) and maintained at this temperature overnight (about 15 to 17 hours). The reactor temperature was then lowered to the value desired and carbon monoxide was then added to the hydrogen stream to give the desired steady-state ratio. The hydrogen-carbon monoxide ratio was determined by gas chromatographic analysis prior to entering the reactor. The total gas flow rate was approximately 7 STP liters/hr. A period of from about 1 to about 2 hours was allowed for the reactor to reach a steady-state at the desired reaction temperature. During the course of a run, one or more effluent gas samples were analyzed for hydrogen, carbon monoxide and volatile hydrocarbons. At the end of a run, the liquid product was collected, and the volume of effluent gas was noted. The liquid product was analyzed by gas chromatography. For runs made in the tubular flow reactor, liquid product was collected by cooling the product containing gas through a cold water condenser at approximately 225 psig and 15° C. and then trapping the liquid product in a Dry Ice-pentanol trap having a capacity of approximately 55 cc. maintained at a temperature of about −80° C. The liquid product from the trap and the condenser were combined to obtain a single liquid sample which was analyzed by gas chromatography.

Succeeding runs with the same catalyst were made either at the same conditions or at new conditions of temperature, feed gas flow rates, etc. If any of the reaction conditions were changed, carbon monoxide flow was shutoff and hydrogen flow was continued until the new set of reaction conditions was reached. The reactor was then allowed to reach a new steady-state following reintroduction of carbon monoxide prior to the beginning of new run.

The following examples serve to provide specific illustrations of the present invention. In the light of the foregoing disclosure numerous modifications are possible in the practice of the present invention without departing from the scope thereof.

EXAMPLE 1

This example illustrates the preparation of a catalyst comprising about 3.0 weight percent rhodium and 6.5 weight percent molybdenum supported on γ-alumina.

A 7.9022 gram sample of ammonium paramolybdate, $(NH_4)_6Mo_7O_{24}.4H_2O$ (obtained commercially from the J. T. Baker Chemical Company, Phillipsburg, N.J. 08865) was dissolved in 50 milliliters of distilled water. The resultant aqueous solution was employed to impregnate 60 grams of γ-alumina (obtained commercially from Rhodia, Inc., P.O. Box 125, Monmouth Junction, N.J. 08852). The impregnated γ-alumina composition was dried at room temperature over the weekend. It was then placed in an oven and dried at 100° C. for about 2 hours. The composition was then calcined by slowly heating the composition from 200° C. up to a temperature of 525° C. over a period of time of about 7 hours and holding the composition at this temperature for about 15 hours. The resultant composition was a γ-alumina support containing approximately 6.5 weight percent molybdenum, probably in the form of $MoO_3$.

Next, a solution was prepared by dissolving 0.7694 grams of rhodium trichloride (40.66% rhodium); obtained commercially from Engelhard Industries Division, Engelhard Materials and Chemicals Corporation, 429 Delancy Street, Newark, N.J. 07105 in 15 milliliters of distilled water. The solution was used to impregnate approximately 10.0 grams of the γ-alumina support containing 6.5 weight percent molybdenum prepared as described above. The co-impregnated γ-alumina composition was dried at room temperature over the weekend. The composition was then placed in an oven and dried at 100° C. for about 2–3 hours. The composition was then mildly reduced by slowly heating the composition from 200° C. to 300° C. over a period of 2–3 hours while flowing hydrogen over the composition. This was followed by calcining the composition at 600° C. overnight (about 13 hours). Finally, the composition was reduced by slowly heating the composition from 200° C. up to 410° C. over a period of 6–7 hours while flowing hydrogen over the catalyst. Reduction was continued at 410° C. overnight. This resulted in a catalyst composition containing about 2.9 weight percent rhodium and about 6.5 weight percent molybdenum.

EXAMPLE 2

Using the above catalyst, pressure and tubular flow reactor, the following runs were made to demonstrate the activity and selectivity of the catalyst for producing dimethyl ether and methanol from synthesis gas. Pressure was maintained at approximately 230 psig; the hydrogen and carbon monoxide ratio was maintained near 2; temperature was varied from about 220° C. to about 280° C. Reaction conditions and product composition data are summarized as Runs 1–3 in Table 1 below.

TABLE 1

Synthesis Gas Reaction on Rh(2.9%)—Mo(6.5%)/—Al$_2$O$_3$ Catalysts

| | Run No. | | |
|---|---|---|---|
| | 1 | 2 | 3 |
| Temp. °C. | 218 | 245 | 277 |
| H$_2$/CO | 2.2 | 2.1 | 2.2 |
| GHSV | 1440 | 1480 | 1570 |
| Pressure;psig | 230 | 231 | 231 |
| CO conversion, % | 3.9 | 20.1 | 35.4 |
| Product Distribution C % | | | |
| CO$_2$ | 17.5 | 30.7 | 32.0 |
| CH$_4$ | 23.4 | 15.8 | 26.2 |
| C$_2$–C$_4$ HC's | — | 3.9 | 8.4 |
| MeOH | 10.6 | 5.1+ | 3.7 |
| EtoH | 1.6 | 1.1 | 1.1 |
| CH$_3$OCH$_3$ | 46.7 | 37.8 | 23.4 |
| CH$_3$OEt | — | 5.5 | 5.3 |

The data shows that the rhodium-molybdenum catalyst was very active for the synthesis gas reaction. Carbon monoxide conversion was 35.4% at 277° C. and selectivity for dimethyl ether and methanol combined approached 58% at 218° C. With all other variables held constant, the selectivity for dimethyl ether and methanol was greater at the lower temperatures studied (i.e. about 50% at 218° C. compared to approximately 27.1% at 277° C.).

EXAMPLE 3

The following runs were made to study the effect on activity and product distribution of the γ-alumina supported rhodium-molybdenum catalyst at a H$_2$/CO ratio of 1.

A γ-alumina supported-molybdenum catalyst having a composition of approximately 3.1% rhodium and 6.3 molybdenum was prepared as follows. A molybdenum modified γ-alumina support was prepared as described in preceeding Example 1.

A solution was prepared by dissolving 1.00 gram of rhodium nitrate (Alpha Products, 152 Andover Street, Danvers, Maine 01923) in 15 milliliters of distilled water. The solution was used to impregnate 10.0 grams of the modified support. The impregnated support was slowly heated over a hot plate set at "Low" for about 2 hours. The composition was then dried in an oven at 100° C. for about 2 hours and then slowly heated up to a final temperature of about 550° C. overnight (about 14 hours). It was then placed in the aforedescribed tubular flow reactor and reduced with hydrogen by flowing hydrogen over the composition for a period of 6–7 hours while slowly increasing the temperature from 200° C.–400° C. The composition was then reduced at 400° C. overnight (about 16 hours). The resultant composition was a γ-alumina supported catalyst containing about 3.1 weight percent rhodium and about 6.3 weight percent molybdenum. The following runs were made to study the effects of passing a hydrogen/carbon monoxide feed stream maintained at a ratio of approximately 1 over the catalyst bed. Reaction conditions and product composition data are summarized as Runs 1 and 2 in Table 2 below.

TABLE 2

Synthesis Gas Reaction on a ν-Alumina Supported Rh(3.1%)—Mo(6.3%) Catalyst H$_2$/CO Molar Ratio = 1

| | Run No. | |
|---|---|---|
| | 1 | 2 |
| Temp. °C. | 246 | 277 |
| H$_2$/CO | 1.30 | 1.08 |
| GHSV | 1220 | 1270 |
| Pressure;psig | 234 | 234 |
| CO Conversion, % Product Distribution | 9.3 | 17.9 |
| CO$_2$ | 36.6 | 40.7 |
| CH$_4$ | 10.0 | 13.9 |
| C$_2$–C$_4$ HC's | 4.7 | 13.7 |
| MeOH | 2.7 | 1.9 |
| EtOH | 0.6 | 0.3 |
| CH$_3$OCH$_3$ | 39.5 | 26.3 |
| CH$_3$OEt | 5.9 | 3.2 |

The data presented in Runs 1 and 2 in Table 2 above indicate that with all other variables held constant, a H$_2$/CO mole ratio of approximately 1 has about the same effect on product composition as a H$_2$/CO mole ratio of 2 for a catalyst composition containing approximately 3.0 weight percent rhodium and approximately 6.0 weight percent molybdenum. This can be seen by comparing Runs 1 and 2 in Table 2 with Runs 2 and 3 in Table 1 above.

EXAMPLE 4

This example demonstrates the higher selectivity for dimethyl ether when the concentration of molybdenum in the catalyst composition is increased to approximately 14.0 weight percent.

A γ-alumina supported rhodium-molybdenum catalyst containing about 3.0 weight percent rhodium and about 14.0 weight percent molybdenum was prepared as follows. An 11.6175 gram sample of ammonium paramolybdate (J. T. Baker Chemical Company) was dissolved in 30 milliliters of distilled water. The solution was heated slightly to dissolve all of the solid. The solution was then added to 30.3 grams of γ-alumina (Rhodia, Inc.) while stirring. The molybdenum modified support was then heated over a hot plate set at the "Low" position until all of the liquid was evaporated. The composition was then dried in an oven at 100° C. for about 2 hours and then calcined overnight at approximately 550° C.

A rhodium nitrate solution was prepared by dissolving 0.997 gram of rhodium nitrate (Alpha Products) in 15 milliliters of distilled water. The solution was then used to impregnate the molybdenum modified γ-alumina support prepared as described above. The resultant composition was a γ-alumina support containing about 14.1 weight percent molybdenum and 3.1 weight percent rhodium. The co-impregnated catalyst composition was then heated over a hot plate until all of the liquid was evaporated. The catalyst was then dried in an oven at 100° C. for about 2 hours and then calcined at 600° C. overnight (about 14 hours). The composition was then reduced with hydrogen at 400° C. for approximately 15 hours.

Using the above catalyst, pressure and tubular flow reactor apparatus, the following runs were made to determine the effect of increasing the molybdenum content of the catalyst composition to about 14.0 weight percent. Reaction conditions and product composition data are summarized as Runs 1 and 2 in Table 3 below.

TABLE 3

Synthesis Gas Reaction on Rh(3.1%)—Mo(14.1%)/ ν-Al₂O₃ Catalysts

|  | Run No. 1 | Run No. 2 |
|---|---|---|
| Temp. °C. | 247 | 276 |
| H₂/CO | 2.2 | 2.1 |
| GHSV | 1600 | 1570 |
| Pressure;psig | 231 | 231 |
| CO conversion, % | 13.2 | 27.8 |
| Product Distribution C% | | |
| CO₂ | 29.7 | 34.4 |
| CH₄ | 11.7 | 17.9 |
| C₂-C₄ HC's | 2.7 | 9.1 |
| MeOH | 4.6 | 3.4 |
| EtOH | 0.4 | 0.2 |
| CH₃OCH₃ | 47.9 | 33.3 |
| CH₃OEt | 3.2 | 1.7 |

By comparing Runs 1 and 2 in Table 3 with Runs 2 and 3 in preceeding Table 1, it can be seen that at approximately the same reaction conditions more dimethyl ether was produced with the catalyst of Example 4 containing approximately 14.1 weight percent molybdenum. A comparison of the data in Tables 1 and 3 shows that at approximately 247° C. dimethyl ether accounted for about 48% of the converted carbon monoxide for the catalyst composition having the higher concentration of molybdenum. Dimethyl ether production at the same temperature using the catalyst composition of Example 1 having a molybdenum content of only 6.5 weight percent, however, accounted for only 38% of the converted carbon monoxide. Thus, both the activity and selectivity for dimethyl ether production was greater for the catalyst having the higher molybdenum content.

EXAMPLE 5

This example demonstrates that iron can be added to the γ-alumina supported rhodium-molybdenum catalyst composition of the present invention without significantly changing the function of the catalyst. A catalyst composition containing about 3.0 weight percent iron, 3.0 weight percent rhodium and 6.0 weight percent molybdenum was prepared as follows.

A molybdenum-modified γ-alumina support was prepared according to the procedure set forth in preceeding Example 1.

A solution was prepared by dissolving 1.0 gram of rhodium nitrate (Alpha Products) and 2.1941 grams of ferric nitrate Fe(NO₃)₃.9H₂O (J. T. Baker Chemical Company) in 15 milliliters of distilled water. A 10 gram quantity of the modified support was co-impregnated with the aqueous solution of rhodium and iron salts. The co-impregnated γ-alumina composition was then slowly dried over a hot plate until all of the liquid was evaporated. The catalyst composition was then dried in an oven at 100° C. for about 2 hours and then calcined by slowly heating the composition from approximately 325° C. up to a final temperature of 560° C. and heating at this temperature overnight. The catalyst was then reduced with hydrogen at 400° C. for approximately 17 hours.

A series of runs were made to determine the activity and selectivity of the rhodium-molybdenum-iron-catalyst. The catalyst was tested in the tubular flow reactor previously described in accordance with the procedure set forth above. Reaction conditions and product composition data are summarized as Runs 1-4 in Table 4 below.

TABLE 4

Synthesis Gas Reaction on ν-Alumina Supported Rh(3.0%)—Iron(3.0%)—Mo(6.0%) Catalyst

|  | Run No. 1 |
|---|---|
| Temp. °C. | 247 |
| H₂/CO | 1.08 |
| GHSV | 1100 |
| Pressure;psig | 235 |
| CO conversion, % | 2.9 |
| Product Distribution C% | |
| CO₂ | 39.7 |
| CH₄ | 8.7 |
| C₂-C₄ HC's | — |
| MeOH | 4.2 |
| EtOH | 1.6 |
| n-PrOH | 0.2 |
| n-BuOH | 0.1 |
| CH₃OCH₃ | 45.5 |

A comparison of the data set forth in Table 4 above with the data set forth in Run No. 1 in preceeding Table 2 indicates that at similar reaction conditions, the addition of 3.0 percent by weight of iron to a catalyst composition containing about 3.0 weight percent rhodium and about 6.0 weight percent molybdenum changes the activity and selectivity of the γ-alumina supported rhodium-molybdenum catalyst very little. As indicated in Table 4, only slightly more dimethyl ether was produced with the iron-containing catalyst, however, CO conversion was significantly less.

EXAMPLE 6

This example demonstrates the higher selectivity for methanol production of the γ-alumina supported rhodium-molybdenum catalyst of the present invention when the synthesis gas reaction is conducted at high pressures.

A γ-alumina supported rhodium-molybdenum catalyst comprising approximately 3.2 weight percent rhodium and 14.6 weight percent molybdenum was prepared according to the following procedure.

A molybdenum-modified-γ alumina support was prepared according to the procedure set forth in preceeding Example 4. A solution was prepared by dissolving 1.8940 grams of rhodium trichloride (Engelhard) in 40 milliliters of distilled water. The solution was used to impregnate a 24.66 gram sample of the molybdenum-modified-γ-alumina. The composition was dried in an oven at 100° C. for about 5 hours. It was then placed in a tubular furnace and reduced with hydrogen at 200° C. for about 1 hour and then at 300° C. overnight (about 15 hours). The composition was then calcined at 570° C. for about 16 hours. Finally, the catalyst composition was reduced with hydrogen at 400° C. for 15 hours. The resultant composition contained about 3.2 weight percent rhodium and 14.6 weight percent molybdenum.

Several runs were made in the Berty reactor, aforedescribed, using the above catalyst at pressures ranging between approximately 800-3000 psig. Approximately 3.7 grams of catalyst was charged to the reactor. Reaction conditions and product composition data are summarized as Runs 1-6 in Table 5 below.

TABLE 5

Synthesis Gas Reaction on Rh(3.2%)—Mo(14.6%) $\nu$-$Al_2O_3$ Catalyst at High Pressure

| | Run No. | | | | | |
|---|---|---|---|---|---|---|
| | 1 | 2 | 3 | 4 | 5 | 6 |
| Temp. °C. | 222 | 220 | 218 | 219 | 218 | 190 |
| $H_2$/CO | 2.0 | 2.0 | 2.0 | 2.0 | 2.0 | 2.0 |
| GHSV | 1220 | 1220 | 1220 | 1220 | 1220 | 1220 |
| Pressure;psig | 855 | 940 | 1505 | 2940 | 2930 | 2920 |
| CO conversion, % | 26.3 | 28.6 | 23.7 | 21.1 | 28.7 | 5.3 |
| Product Distribution C% | | | | | | |
| $CO_2$ | 26.3 | 24.1 | 19.7 | 17.5 | 15.6 | 17.6 |
| $CH_4$ | 13.5 | 10.0 | 9.0 | 9.8 | 8.8 | 10.2 |
| $C_2$-$C_4$ HC"s | 4.2 | 3.6 | 2.9 | 2.6 | 2.2 | 2.2 |
| MeOH | 32.9 | 38.6 | 45.5 | 53.0 | 55.4 | 54.5 |
| EtOH | 4.0 | 4.8 | 5.6 | 6.3 | 6.5 | 6.5 |
| n-PrOH | 0.7 | 1.1 | 1.5 | 2.0 | 2.1 | 2.2 |
| $CH_3COOCH_3$ | 0.4 | — | 0.2 | 0.2 | 0.1 | — |
| $CH_3COOEt$ | — | — | — | 0.3 | 0.4 | — |
| $CH_3OCH_3$ | 17.2 | 16.4 | 13.7 | 6.6 | 6.4 | 5.1 |
| $CH_3OH$ + $CH_3OCH_3$ | 50.1 | 55.0 | 59.2 | 59.6 | 61.8 | 59.6 |

As shown by the data in Table 5 above, at higher pressures, the selectivity of the catalyst changes to favor methanol production over dimethyl ether production. The activity at 220° C. and 2930 psig was as high as 55.4% for methanol while dimethyl ether activity dropped to about 6.4%. This may be attributed to the greater stability of methanol at higher pressures than dimethyl ether. If both methanol and dimethyl ether are considered together as one product, their yield was above 50% for each run and was as high as 61.8% at 2930 psig.

Claims to the invention follow.

What is claimed is:

1. Catalyst composition for selectively converting gaseous mixtures of carbon monoxide and hydrogen to dimethyl ether and methanol, said catalyst consisting essentially of rhodium, molybdenum and iron supported on alumina.

2. The composition of claim 1 containing about 0.1 weight percent to about 10.0 weight percent rhodium, about 1.0 weight percent to about 30 weight percent molybdenum and about 3.0 weight percent iron based upon the total weight of the composition.

3. The composition of claim 1 wherein said alumina support is selected from the group consisting of alpha alumina, eta alumina and gamma alumina.

* * * * *